(12) United States Patent
Frick et al.

(10) Patent No.: US 10,939,832 B2
(45) Date of Patent: Mar. 9, 2021

(54) DEVICE AND METHOD FOR MEASURING BLOOD PRESSURE AND FOR INDICATION OF THE PRESENCE OF ATRIAL FIBRILLATION

(71) Applicants: Microlife Intellectual Property GmbH, Widnau (CH); Joseph Wiesel, West Hempstead, NY (US)

(72) Inventors: Gerhard Frick, Feldkirch (AT); Joseph Wiesel, West Hempstead, NY (US)

(73) Assignee: MICROLIFE INTELLECTUAL PROPERTY GMBH, Widnau (CH)

( * ) Notice: Subject to any disclaimer, the term of this patent is extended or adjusted under 35 U.S.C. 154(b) by 479 days.

(21) Appl. No.: 14/619,794

(22) Filed: Feb. 11, 2015

(65) Prior Publication Data
US 2016/0228017 A1    Aug. 11, 2016

(51) Int. Cl.
*A61B 5/022*    (2006.01)
*A61B 5/0235*    (2006.01)
*A61B 5/00*    (2006.01)

(52) U.S. Cl.
CPC .......... *A61B 5/02233* (2013.01); *A61B 5/022* (2013.01); *A61B 5/0235* (2013.01); *A61B 5/02225* (2013.01); *A61B 5/6824* (2013.01); *A61B 5/7246* (2013.01); *A61B 5/7278* (2013.01); *A61B 5/7264* (2013.01)

(58) Field of Classification Search
CPC combination set(s) only.
See application file for complete search history.

(56) References Cited

U.S. PATENT DOCUMENTS

| 4,356,827 A | 11/1982 | Uemura et al. |
| 6,746,403 B2 | 6/2004 | Kolluri et al. |

(Continued)

FOREIGN PATENT DOCUMENTS

| EP | 1195133 A2 | 4/2002 |
| EP | 1858407 B1 | 11/2013 |

OTHER PUBLICATIONS

Verberk, Willem J., and Peter W. de Leeuw. "Accuracy of oscillometric blood pressure monitors for the detection of atrial fibrillation: a systematic review." Expert review of medical devices 9.6 (2012): 635-640.*

(Continued)

*Primary Examiner* — Christian Jang
*Assistant Examiner* — Mitchell E Alter
(74) *Attorney, Agent, or Firm* — Davis & Bujold PLLC; Michael J. Bujold

(57) ABSTRACT

A device for measuring blood pressure and for indicating the presence of atrial fibrillation, includes an inflatable cuff, a pump, at least one pressure sensor for measuring the pressure inside the cuff, a pressure relief valve for deflating the cuff, and a control unit for controlling the pump and the valve. A calculating unit determines the presence or absence of atrial fibrillation on the basis of pressure variation sensed by the sensor. The calculating unit is adapted to independently determine the presence of atrial fibrillation on the basis of at least one, preferably two sequences, of pulse beats. The control unit is configured to maintain the pressure in a predefined range or to restore the pressure to a predefined range for an additional sequence, and to determine the presence of atrial fibrillation only if the calculating unit determines the presence of atrial fibrillation during a first and/or preceding sequence.

7 Claims, 3 Drawing Sheets

(56) References Cited

U.S. PATENT DOCUMENTS

| | | | | |
|---|---|---|---|---|
| 2004/0171943 | A1* | 9/2004 | Hersh | A61B 5/02225 600/490 |
| 2006/0155196 | A1* | 7/2006 | Ramsey | A61B 5/02141 600/490 |
| 2006/0195037 | A1* | 8/2006 | Wiesel | A61B 5/024 600/518 |
| 2007/0106163 | A1* | 5/2007 | Friedman | A61B 5/02125 600/485 |
| 2009/0137912 | A1 | 5/2009 | Hirabara et al. | |
| 2013/0060152 | A1* | 3/2013 | Baron | A61B 5/02116 600/494 |

OTHER PUBLICATIONS

Marazzi, Giuseppe, et al. "Comparison of Microlife BP A200 Plus and Omron M6 blood pressure monitors to detect atrial fibrillation in hypertensive patients." Advances in therapy 29.1 (2012): 64-70. (Year: 2012).*

Wiesel, Joseph, Benjamin Arbesfeld, and David Schechter. "Comparison of the Microlife blood pressure monitor with the Omron blood pressure monitor for detecting atrial fibrillation." The American journal of cardiology 114.7 (2014): 1046-1048. (Year: 2014).*

International Search Report issued in corresponding International Patent Application No. PCT/EP2016/050150 dated Feb. 24, 2016.

Joseph Wiesel, MD, Saji Abraham, MD, and Frank C. Messineo, MD, Screening for Asymptomatic Atrial Fibrillation While Monitoring the Blood Pressure at Home: Trial of Regular Versus Irregular Pulse for Prevention of Stroke (TRIPPS 2.0), Department of Cardiology, North Shore University Hospital, Manhasset, New York, Manuscript received and accepted Jan. 27, 2013, pp. 1598-1601.

Circulation, vol. XLI, Bert K. Bootsma, MD, Adriaan J. Hoelen, M.SC., Jan Strackee, Ph.D., and Frits L. Meijler, MD, Analysis of R-R Intervals in Patients with Atrial Fibrillation at Rest and During Exercise, May 1970, pp. 783-794.

* cited by examiner

DEVICE AND METHOD FOR MEASURING BLOOD PRESSURE AND FOR INDICATION OF THE PRESENCE OF ATRIAL FIBRILLATION

FIELD OF THE INVENTION

The present invention relates to a device and a method for measuring blood pressure and for indication of the presence of atrial fibrillation according to the independent claims.

BACKGROUND OF THE INVENTION

The heart is the major muscle that functions as the primary pump for blood flow throughout the body. The heart contains two upper chambers called atria and two lower chambers called ventricles. The right atrium receives oxygen-depleted blood while the left atrium receives blood enriched with oxygen from the lungs. When the atria are full, the valves within the heart open and the atria squeezes blood into the ventricles. The right ventricle then pumps oxygen-depleted blood into the lungs whereas the left ventricle pumps oxygen-enriched blood to all parts of the body. In this fashion, the heart functions primarily as a double sided pump.

The heart's internal pacemaker, known as the sinus node, signals the start of each heartbeat. This signal originates in the right atrium in the sinoatrial node and travels simultaneously to the left atrium and down into the interatrial septum to the atrio-ventricular node. The cycle of electrical stimulation that normally occurs is referred to as normal sinus rhythm. The contraction of the ventricles will be referred to as the heartbeats.

There may be several rhythm abnormalities present. One of the rhythm abnormalities is atrial fibrillation in which the atria do not contract normally. Instead, there is a continuously varying pattern of electrical activation of the atria resulting in a rapid, highly irregular pattern of impulses reaching the atrioventricular node. The atrioventricular node acts as a filter and allows a reduced number of these impulses to reach the ventricles which results in a highly irregular heartbeat pattern. This irregular pattern has been shown in previous studies to be a random pattern (Bootsma et al: Analysis of R—R intervals in patients with atrial fibrillation at rest and during exercise. Circulation 41:783, 1970).

Devices and methods have been developed to determine presence of atrial fibrillation for example by photoplethysmographic systems or by devices for measuring blood pressure.

In EP 1 858 407 an apparatus is disclosed which enables determination of atrial fibrillation out of a sequence of pulse beats. Clinical studies using the apparatus disclosed in EP 1 858 407 have shown good accuracy for detecting atrial fibrillation with one reading. However, taking more than one reading further improves the accuracy for detecting atrial fibrillation (Wiesel et. al. Am J Cardiology 2013; 111:1598-1601). These two readings were taken during two separate inflation and deflation cycles, which made the measurement uncomfortable for the patient.

SUMMARY OF THE INVENTION

It is therefore an object of the present invention to create a more accurate, and at the same time, comfortable device and to present a method for measuring blood pressure and for indicating the presence of atrial fibrillation or the absence of atrial fibrillation.

The object is accomplished by a device for measuring blood pressure and for indicating the presence of atrial fibrillation and corresponding method according to the independent claims.

In particular, the object is accomplished by a device for measuring blood pressure and for indicating the presence of atrial fibrillation. The device comprises an inflatable cuff adapted to be wrapped around an extremity of a patient, a pump for inflating said cuff, at least one pressure sensor for measuring the pressure inside the cuff, a pressure release valve for deflating said cuff, a control unit for controlling operation of said pump and of said pressure release valve, a calculating unit for determining the presence or absence of atrial fibrillation on the basis of pressure variations sensed with said sensor. A calculation unit is adapted to independently determine the presence of atrial fibrillation on the basis of at least one, preferably two sequences of pulse beats. The control unit is further configured to maintain said pressure in a predefined range or to restore said pressure to a predefined range for an additional sequence and to determine the presence of atrial fibrillation only if the calculating unit determine the presence of atrial fibrillation during a first and/or a preceding sequence, preferably during all preceding sequences.

A sequence according to the present invention is the minimum number of heart beats that allow for the determination of the presence or absence of atrial fibrillation as an intermediate or final result by the calculating unit.

The preceding sequence according to the present invention is a sequence in which atrial fibrillation is determined which precedes, preferably directly precedes, the next sequence.

The extremity of a patient preferably is the arm, more preferably the upper arm.

The device, according to the present invention, only continues taking measurements after the first sequence of pulse beats is determined to show atrial fibrillation. Hence, in case where the first sequence does not show atrial fibrillation, the measurements will stop and the patient will not have to wait for anymore measurements. This leads to a more comfortable measurement.

The object is further accomplished by a device for measuring blood pressure and for indicating the presence of atrial fibrillation. This device comprises an inflatable cuff adapted to be wrapped around an extremity of a patient, a pump for inflating said cuff, at least one pressure sensor for measuring the pressure inside the cuff, a pressure release valve for deflating said cuff, control unit for controlling operation of said pump and of said pressure release valve, a calculating unit for determining the presence or absence of atrial fibrillation on the basis of pressure variations sensed with said sensor. A calculating unit is adapted to independently determine the presence of atrial fibrillation on the basis of at least two, preferably three sequences, of pulse beats and the control unit is configured to maintain the pressure within the cuff within a range sufficient to determine atrial fibrillation during said at least two sequences without substantially decreasing or increasing the pressure between said sequences.

By applying at least two sequences without substantially decreasing or increasing the pressure between said sequences the accuracy of the determination of the presence of atrial fibrillation is significantly enhanced. Further, the risk of the patient removing the cuff is reduced, since the patient understands that the measurement is still ongoing when the cuff remains inflated.

In both of the previously described devices, the control unit can be configured to relieve the pressure from the cuff or continue to inflate the cuff in order to determine the blood pressure after the calculating unit has determined the absence of atrial fibrillation in a first or second sequence.

Such a device enables fast measurement of the blood pressure and the determination of atrial fibrillation in one device.

The calculating unit can be adapted to determine the presence or absence of atrial fibrillation on the basis of pressure variation sent within said sensor during a third sequence, only if the presence of atrial fibrillation has been determined in the first and in the second sequence.

This device leads to a more accurate determination of the presence of atrial fibrillation and to shorten measurement times in case the absence of atrial fibrillation has been determined.

The pressure relief valve can be a controllable valve, preferably an electronic or linear valve.

The use of a controllable valve leads to the possibility of precisely controlling the inflation and deflation, of the cuff and thereby leads to the possibility of analyzing several sequences of pulse beats for atrial fibrillation without the patient even recognising that multiple sequences were analyzed. Thereby, the risk of the patient removing the cuff too early is reduced.

The sequence can be defined by a predetermined number of pulse beats or by a predetermined time.

The definition of a sequence by a predetermined number of pulses or a predetermined time ensures that it is possible to determine the presence or absence of atrial fibrillation while the measurement is kept as short as possible.

The calculating unit can comprise means for ascertaining a mean of a succession of time intervals corresponding to that of a sequence of pulse beats and for determining upper and lower boundary levels at a respective percentage of said mean. Additionally, the calculating unit can comprise means configured to recalculate a mean and to calculate a standard deviation of the succession of time intervals that are between the lower and upper boundary values only, without regard to those time intervals that are less than the lower boundary or more than the upper boundary. Additionally a calculating unit can comprise means for determining possible atrial fibrillation based upon a quotient formed by dividing such standard variation by said recalculated mean and comparing the quotient with a threshold value.

The use of these means lead to an accurate determination of the presence of atrial fibrillation in a sequence.

The complete device and a method for determining atrial fibrillation within one sequence is disclosed in EP 1 858 407 which is incorporated by reference in its entirety. In particular, the algorithm disclosed in EP 1 858 407 is incorporated into this application.

A device using this calculating unit leads to more accurate determination of the presence of atrial fibrillation.

As a matter of course even other algorithms can be used.

The calculation unit can be connected to the control unit by a wired connection or by a wireless connection. Additionally, the calculation unit can be implemented in a separate device such as a mobile phone, smart watch or computer. In case of a wired connection the calculation unit can be integrated in a common housing with the control unit of a blood pressure measurement device, the pump and the pressure sensor.

The device further can comprise a display on which the result of the determination of presence of atrial fibrillation is displayed. The display may be integrated in the housing or the display may be part of another device which is able to communicate with the control unit and/or the calculation unit.

The object of the invention is further accomplished by a method for measuring blood pressure and for indication of the presence of atrial fibrillation comprising the following steps:
  providing a device for measuring blood pressure having a cuff, preferably a device as previously described,
  wrapping the cuff around an extremity of a patient,
  inflating the cuff,
  measuring the pressure inside a cuff during at least one sequence,
  determining the presence or absence of atrial fibrillation on the basis of pressure variations inside the cuff preferably by a calculation unit in the device, on the basis of at least two sequences, of a defined number of pulse beats and
  maintaining the pressure within the cuff within a range sufficient to determine atrial fibrillation during said at least two sequences without substantially decreasing or increasing said pressure.

This method leads to a more accurate determination of the presence of atrial fibrillation.

The object of the invention is further accomplished by a method for measuring blood pressure and for indication of the presence of atrial fibrillation comprising the following steps:
  providing a device for measuring blood pressure having a cuff, preferably a device as previously described,
  wrapping the cuff around an extremity of a patient,
  inflating the cuff,
  measuring the pressure inside the cuff during at least one sequence,
  determining the presence or absence of atrial fibrillation on the basis of pressure variations inside the cuff, preferably by a calculation unit within said device on the basis of at least one, preferably two sequences, of a defined number of pulse beats and
  maintaining the pressure within the cuff within a range sufficient to determine atrial fibrillation during said at least one sequence,
  maintaining or restoring said pressure for an additional sequence and determining presence or absence of atrial fibrillation only if the calculation unit determined the presence of atrial fibrillation during the first and/or preceding sequence.

Such a method leads to a more accurate determination of the presence of atrial fibrillation and less false positive results.

In both methods the pressure can be released from the cuff, or further increased, in order to determine the blood pressure if the absence of atrial fibrillation is determined in the first or second sequence.

Hence, the time of measurement for the patient is reduced by ending the measurement in case the absence of atrial fibrillation has been determined.

The presence or absence of atrial fibrillation can be determined on the basis of pressure variations since with said sensor during a third sequence, only if the presence of atrial fibrillation has been determined in the first and in the second sequence.

A third sequence is only obtained if both preceding sequences indicate the presence of atrial fibrillation.

Hence, the measuring time is only extended if at least the first two sequences determined the presence of atrial fibrillation.

The sequence can be defined by predetermined number of pulse speeds or by a predetermined time.

This way it is ensured that the calculating unit receives enough data to determine the presence or absence of atrial fibrillation.

The mean of a succession of time intervals corresponding to that of a sequence can be ascertained and an upper and lower boundary value of the respective percentage of said mean can be determined. A mean is recalculated and a standard deviation of the succession of time intervals can be recalculated that are at or between the lower and upper boundary values only, without regard to those time intervals that are less than the lower boundary or more than the upper boundary, and possible atrial fibrillation can be determined based upon a quotient formed by dividing said standard deviation by said recalculated mean and comparing the quotient with a threshold value.

This way the presence of atrial fibrillation can be determined in an easy and reliable way.

The object of the invention is further accomplished by a device for measuring blood pressure and for indicating the presence of atrial fibrillation. The device comprises an inflatable cuff adapted to be wrapped around an extremity of a patient, a pump for inflating said cuff, at least one pressure sensor for measuring the pressure inside the cuff, the pressure relief valve for deflating said cuff, a control unit for controlling operation of said pump and of said pressure relief valve, and a calculating unit for determining the presence or absence of atrial fibrillation on the basis of pressure variation sensed within said sensor. The calculating unit is adapted to independently determine the presence of atrial fibrillation on the basis of at least one, preferably two sequences, of pulse beats and the control unit is configured to maintained such pressure in predefined range or restore said pressure to a predefined range until the calculating unit determines the presence or absence of atrial fibrillation.

This device enables an accurate determination of the presence of atrial fibrillation using a blood pressure measuring device.

On all previously described methods and devices, blood pressure measurements can be conducted and displayed simultaneously with the results of determination of the presence or absence of atrial fibrillation.

BRIEF DESCRIPTION OF THE DRAWINGS

The invention is shown in the following embodiments by means of examples.

DESCRIPTION OF THE PREFERRED EMBODIMENTS

Figure 1:
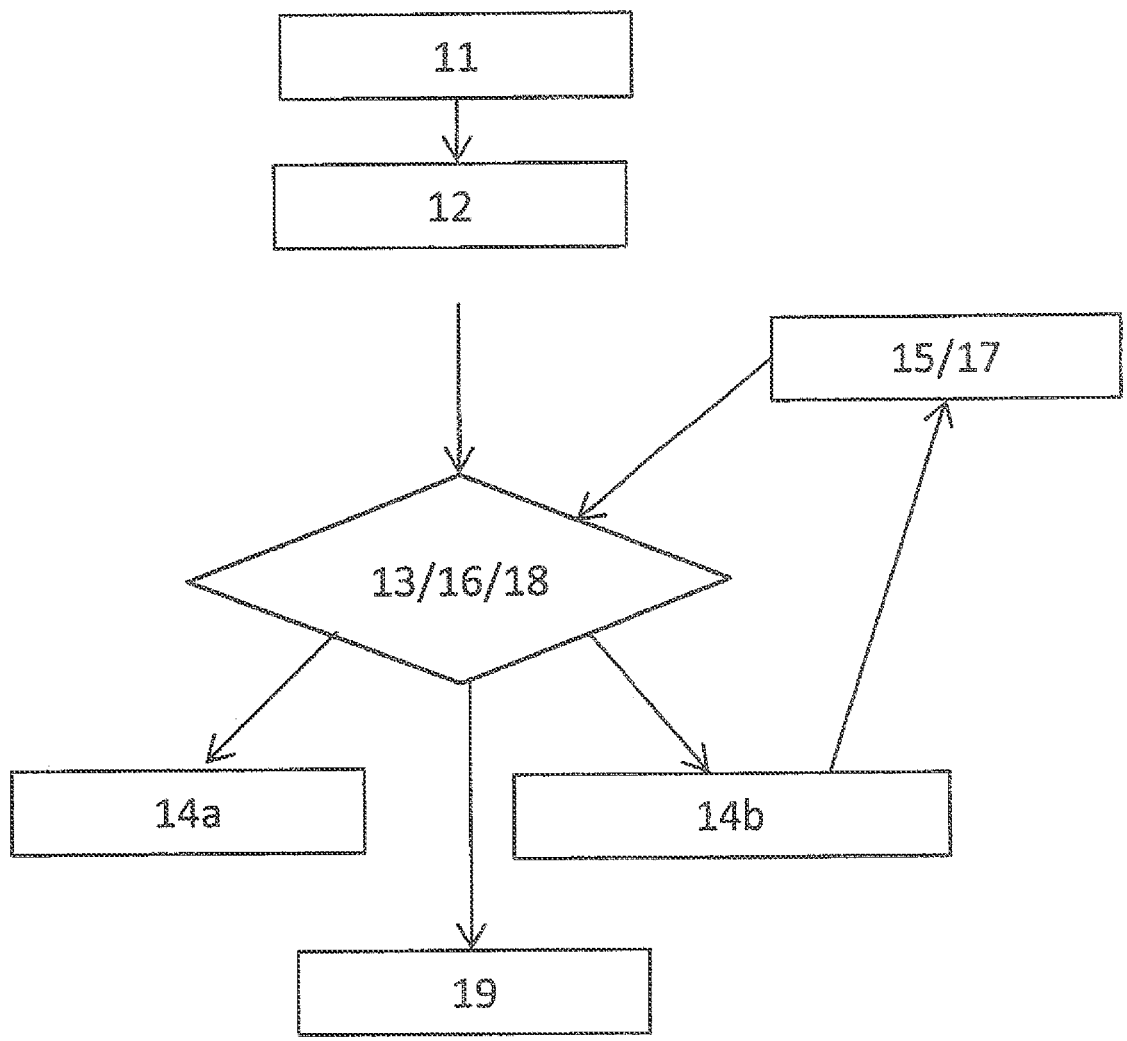
FIG. 1 A schematic flow diagram of a first embodiment of the invention

FIG. 1 shows a schematic flow diagram of the method for measuring blood pressure and for indicating of the presence of atrial fibrillation in a first embodiment. In a first step 11 the cuff is inflated. The speed of the inflation is controlled by the control unit 6 (see FIG. 3) such that it is possible to analyze a first sequence 12 of pulse beats while the cuff 2 is still inflated. The only prerequisite is that the pressure is above a certain level to be able to obtain a sequence. Based on the first sequence 12 the presence or absence of atrial fibrillation is determined in step 13. If the absence of atrial fibrillation is determined in step 13 this information is displayed to the patient. Based on this first determination that atrial fibrillation is absent, cuff 2 is deflated in step 14a. If atrial fibrillation was determined to be present in step 13, the pressure in the cuff is maintained or restored to the necessary level and a second sequence 15 is obtained. Based on the second sequence, the presence or absence of atrial fibrillation in step 16 is determined once more. The second sequence in step 15 is analyzed in step 16. If it is determined that atrial fibrillation is absent in step 16 the cuff 2 is deflated in step 14a. The absence of atrial fibrillation is displayed to the patient. If atrial fibrillation is determined to be present in step 16 the pressure in the cuff 2 is maintained or restored in step 14b and a third sequence is obtained in step 17. In the sequence of step 17 the presence or absence of atrial fibrillation is determined once more in step 18. After obtaining the third sequence, the cuff is deflated in step 19. In case analysis of the third sequence in step 17 determines that atrial fibrillation is present in step 18 the final result of the presence of atrial fibrillation is displayed to the user. In case analysis of the sequence of step 17 determines the absence of atrial fibrillation in step 18 then the result of the absence of atrial fibrillation is displayed to the user. Optionally, during deflation a blood pressure measurement can be displayed.

A sequence is either defined by a predetermined number of pulse beats, such as 11 beats or by a predetermined time such as 15 seconds. The deflation of the cuff is conducted by a pressure relief valve which is a linear valve which is controllable with respect to the speed of the release of the pressure. Of course, the cuff 2 is wrapped around the arm of a patient before the inflation of the cuff 2 and removed from the arm of the patient after the last deflation. The presence or absence of atrial fibrillation is determined on the basis of pressure variations inside the cuff 2. To be able to determine pressure variations inside the cuff certain pressure has to be present, for example a pressure of 50 mmHg. It is possible to slow down the inflation and the deflation of the cuff especially the inflation and the deflation above a certain pressure level where pressure variations still can be sensed within the cuff 2. The blood pressure measurement is conducted as an oscillometric measurement.

Figure 2:
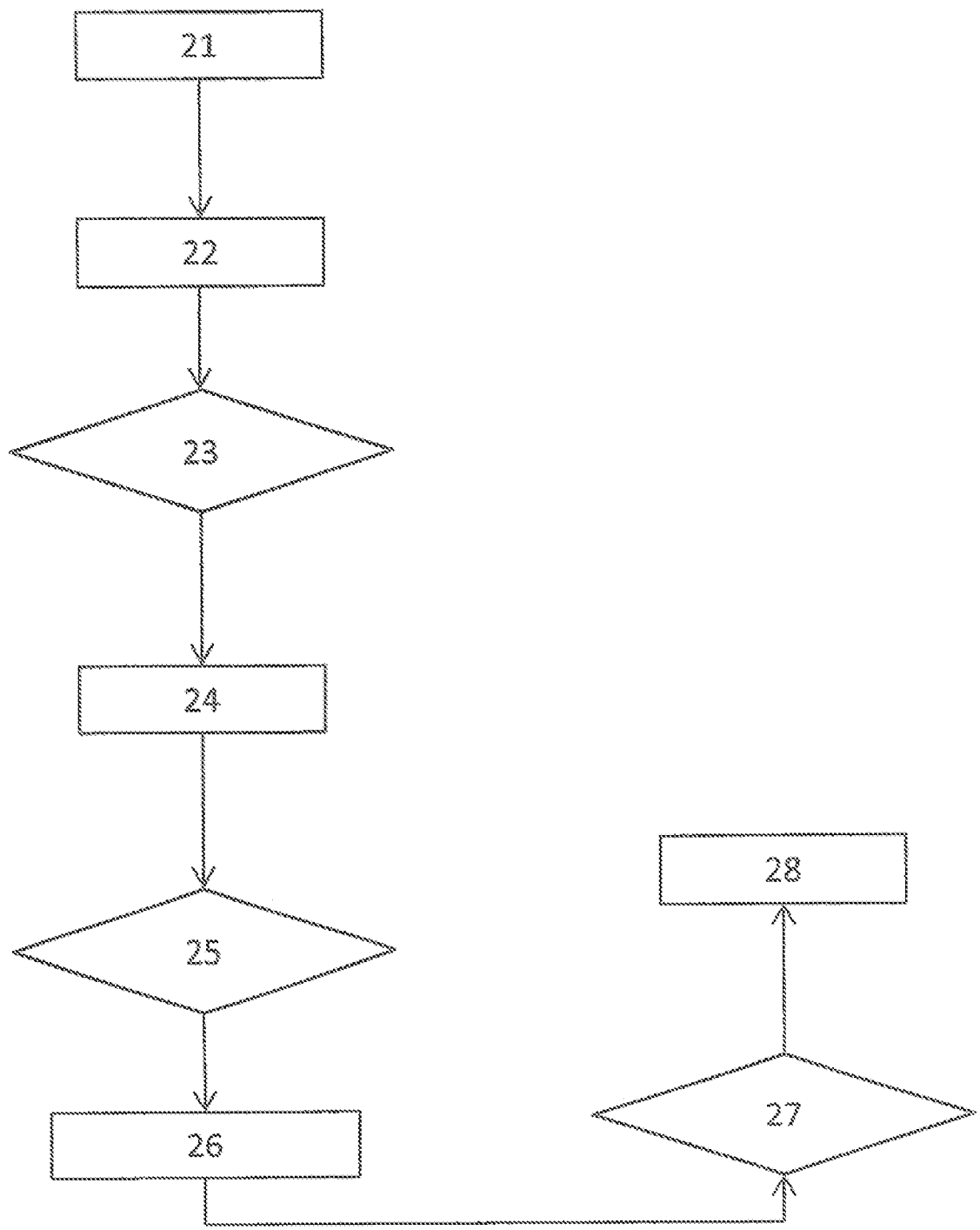
FIG. 2 A schematic flow diagram of a second embodiment of the invention

FIG. 2 shows a schematic flow chart of a second embodiment of the invention. In a first step 21 the cuff 2 (see FIG. 3), which has been wrapped around an arm of a patient, is inflated. After the inflation has reached a predefined pressure level in which pressure variations can be sensed, in step 22 a first sequence is obtained. Based on this first sequence in step 23 the presence or absence of atrial fibrillation is determined. Independent from the result in step 23, in step 24 a second sequence is obtained and based on this second sequence in step 25 the presence or absence of atrial fibrillation is determined. After that, in a third sequence in step 26 the presence or absence of atrial fibrillation is determined in step 27. After all three sequences in step 28, the cuff is deflated and can be removed from the arm of the patient. Optionally, during deflation a blood pressure measurement can be displayed. A positive result for the presence of atrial fibrillation is displayed to the patient only if all three sequences 22, 24 and 26 led to a positive result for the presence of atrial fibrillation in the determination step 23, 25 and 27. It is possible to slow down the inflation and the deflation of the cuff especially the inflation and the deflation above a certain pressure level where pressure variations still can be sensed within the cuff 2. This way, the patient has a feeling that the machine is working and will not remove the cuff believing that the high pressure takes too long and the machine is not working properly.

Figure 3:
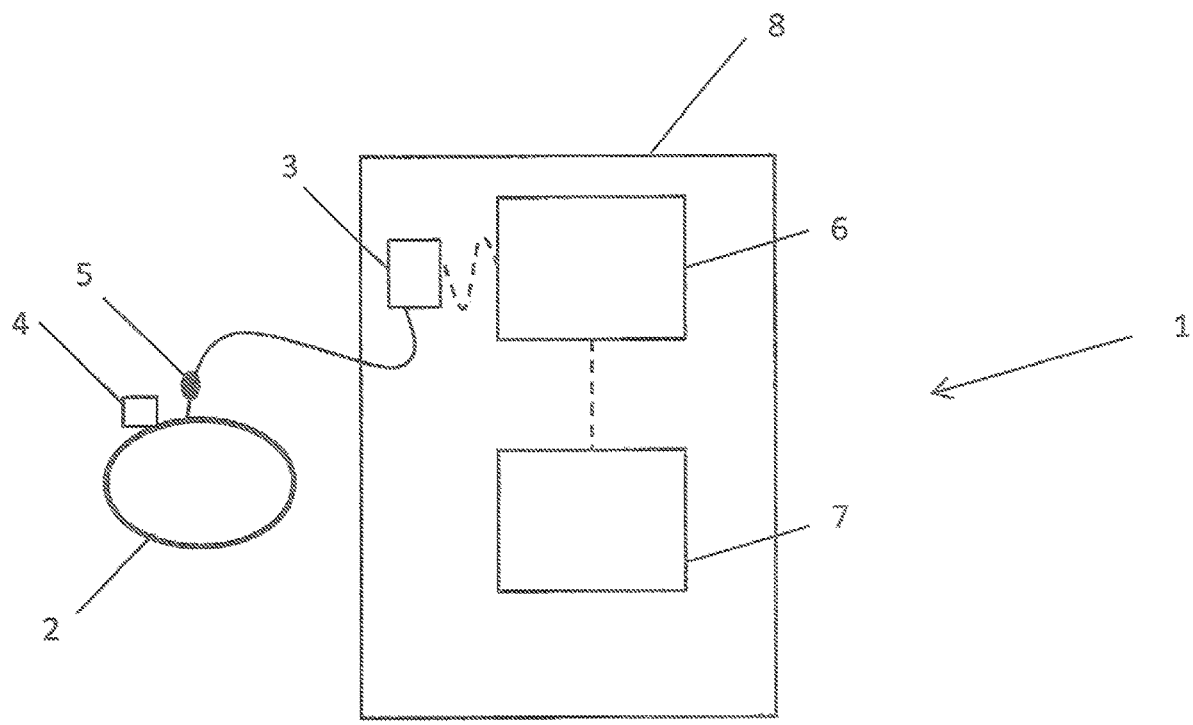
FIG. 3 A schematic representation of a device according to the invention.

FIG. 3 shows a schematic representation of a device 1 according to the invention. The device 1 comprises a cuff 2 to be wrapped around an arm of a patient. The cuff 2 is inflatable such that the cuff 2 circumferentially presses against the arm. Simultaneously, the pressure level inside the cuff 2 is increased. For increasing the pressure in the cuff 2, a pump 3 is in fluid connection with the cuff 2. The pressure sensor 4 measures the pressure inside the cuff 2. The pressure is measured continuously. For releasing the pressure from the cuff 2, the pressure release valve 5 is arranged directly at the cuff 2 or at a fluid connection to the inner area of the cuff 2. The pressure release valve 5 is a linear valve. Additionally, the pressure release valve 5 is controllable by control unit 6. The control unit 6 further controls the pump 3 and is wirelessly or wiredly connected to the pressure sensor 4. Data from the pressure sensor 4 is sent to calculating unit 7 by means of which the presence or absence of atrial fibrillation is determined based on pressure variations inside the cuff 2. The calculating unit 7 is connected to the control unit 6. Calculating unit 7 and control unit 6 are arranged in a common housing 8. From the control unit 6 through housing 8 there is a connection to pump 3 such that the pump 3 can be controlled and does not need an additional energy source. The energy is delivered from control unit 6. Furthermore, the cuff 2 is exchangeable such that the cuff can be substituted when damaged or adapted to another size based on the size of the patient. The device 1 can apply either of the methods shown in FIGS. 1 and 2.

The invention claimed is:

1. A device for indicating a presence of atrial fibrillation, the device comprising:
   an inflatable cuff adapted to be wrapped around an extremity of a patient,
   a pump for inflating said cuff,
   at least one pressure sensor for measuring a pressure inside the cuff,
   a pressure release valve for deflating said cuff,
   a control unit for controlling operation of said pump and of said pressure release valve upon instruction by a calculating unit,
   the calculating unit being configured for:
      determining the presence or absence of atrial fibrillation on a basis of at least one sequence of pulse beats sensed by said at least one pressure sensor and adapting the number of sequences on which the measurement is based according to the determination of absence of atrial fibrillation,
      automatically stopping the measurement if the absence of atrial fibrillation is determined,
      continuing the measurement for at least an additional measurement only if the presence of atrial fibrillation is determined during an initial measurement; and
      instructing the control unit to inflate, to maintain, and to deflate the pressure inside said cuff based on the results of the previous measurement;
   the pump inflating said cuff, and the sensor measuring a first sequence of pulse beats,
   the calculating unit determining the presence of atrial fibrillation based on said first sequence of pulse beats if said first sequence of pulse beats is over the threshold value of atrial fibrillation,
   the calculating unit instructing the control unit to maintain the pressure inside said cuff only if the presence of atrial fibrillation is determined by the calculating unit based on said first sequence of pulse beats, otherwise
   the calculating unit instructing the control unit to decrease the pressure inside said cuff via activating said pressure release valve and discontinuing the measurement since the calculating unit does not determine the presence of atrial fibrillation based on the first sequence of pulse beats;
   the sensor measuring a second sequence of pulse beats only if the calculating unit determines the presence of atrial fibrillation based on the first sequence of pulse beats,
   the calculating unit determining the presence of atrial fibrillation based on said second sequence of pulse beats if the threshold value of atrial fibrillation is reached by said second sequence of pulse beats,
   the calculating unit instructing the control unit to maintain the pressure inside said cuff only if the presence of atrial fibrillation is determined by the calculating unit based on said second sequence of pulse beats, otherwise
   the calculating unit instructing the control unit to decrease the pressure inside said cuff via activating said pressure release valve and discontinuing the measurement since the calculating unit did not determine the presence of atrial fibrillation,
   the sensor measures a third sequence of pulse beats only if the calculating unit determines the presence of atrial fibrillation based on said second sequence of pulse beats,
   the calculating unit being configured to determine the presence of atrial fibrillation based on said third sequence of pulse beats, and
   the calculating unit instructing the control unit to decrease the pressure inside said cuff via activating said pressure release valve and discontinuing the measurement after said third sequence of pulse beats has been measured
   wherein a sequence is defined by a predetermined number of pulse beats or by a predetermined time period and the calculating unit only indicates the presence of atrial fibrillation when the first, the second and the third sequence of pulse beats each indicate atrial fibrillation.

2. The device according to claim 1, wherein the control unit is configured to release the pressure from the cuff, or further increase in order to determine blood pressure if and after the calculating unit determined the absence of atrial fibrillation during a first or a second sequence.

3. The device according to claim 1, wherein the calculating unit is adapted to determine the presence or absence of atrial fibrillation on the basis of pressure variations sensed with said at least one pressure sensor during the third sequence, only if the presence of atrial fibrillation has been determined during the first and during the second sequence.

4. The device according to claim 1, wherein the calculating unit is configured to:
   ascertain a mean of a succession of time intervals between pulse beats corresponding to that of a sequence;
   determine upper and lower boundary values as a respective percentage of said mean;
   recalculate a mean;
   calculate a standard deviation of the succession of time intervals that are at or between the lower and upper boundary values only, without regard to those time intervals that are less than the lower boundary or more than the upper boundary, and determine possible atrial fibrillation based upon a quotient formed by dividing said standard deviation by said recalculated mean and comparing the quotient with a threshold value.

5. A method for indicating a presence of atrial fibrillation, the method comprising the steps of:
providing an inflatable cuff adapted to be wrapped around an extremity of a patient;
providing a pump for inflating said cuff;
providing at least one pressure sensor for measuring the pressure inside the cuff;
providing a pressure release valve for deflating said cuff;
providing a control unit for activation of said pump and said pressure release valve upon instruction by a calculating unit;
the calculating unit being configured to:
determine the presence or absence of atrial fibrillation on the basis of at least one sequence of pulse beats sensed by said sensor and adapt the number of sequences on which the measurement is based according to the determination of absence of atrial fibrillation;
automatically stop the measurement for at least an additional measurement only if the absence of atrial fibrillation is determined;
continue the measurement if the presence of atrial fibrillation is determined for at least one more measurement; and
instruct the control unit to inflate, to maintain; and to deflate the pressure inside said cuff based on the results of a previous measurement;
inflating said cuff and measuring a first sequence of pulse beats via said sensor;
determining the presence of atrial fibrillation via the calculating unit based on said first sequence of pulse beats if said first sequence of pulse beats is calculated to be over a threshold value of atrial fibrillation;
the calculating unit instructing the control unit to maintain the pressure inside said cuff only if the presence of atrial fibrillation is determined by the calculating unit based on said first sequence of pulse beats;
otherwise the calculating unit instructing the control unit to decrease the pressure inside said cuff by activating said pressure release valve and discontinuing the measurement since the calculating unit did not determine the presence of atrial fibrillation based on the first sequence of pulse beats;
measuring a second sequence of pulse beats via the sensor only if the calculating unit determines the presence of atrial fibrillation based on said first sequence of pulse beats;
the calculating unit determining the presence of atrial fibrillation based on said second sequence of pulse beats if said second sequence is calculated to be over the threshold value of atrial fibrillation;
the calculating unit instructing the control unit to maintain the pressure inside said cuff only if the presence of atrial fibrillation is determined by the calculating unit based on said second sequence of pulse beats;
otherwise the calculating unit instructing the control unit to decrease the pressure inside said cuff by activating said pressure release valve and discontinuing the measurement since the calculating unit did not determine the presence of atrial fibrillation based on said second sequence of pulse beats;
measuring a third sequence of pulse beats via the sensor only if the calculating unit determines the presence of atrial fibrillation based on said second sequence of pulse beats;
the calculating unit determining the presence of atrial fibrillation based on said third sequence of pulse beats if said third sequence is calculated to be over the threshold value of atrial fibrillation;
the calculating unit instructing the control unit to decrease the pressure inside said cuff by activating said pressure release valve and discontinuing the measurement after said third sequence of pulse beats has been measured, wherein a sequence is defined by a predetermined number of pulse beats or by a predetermined time period and the calculating unit only indicates the presence of atrial fibrillation when the first, the second and the third sequence of pulse beats each indicate atrial fibrillation.

6. The method according to claim 5, wherein the pressure in said cuff is further increased in order to determine blood pressure if the presence of atrial fibrillation is not determined during a first or a second sequence.

7. The method according to claim 5, wherein a mean of a succession of time intervals corresponding to that of a sequence is ascertained and an upper and a lower boundary value as a respective percentage of said mean is determined and a mean is recalculated and a standard deviation of the succession of time intervals is calculated that are at or between the lower and upper boundary values only without regard to those time intervals that are less than the lower boundary or more than the upper boundary, and a possible atrial fibrillation is determined based upon a quotient formed by dividing said standard deviation by said recalculated mean and comparing the quotient with a threshold value.

* * * * *